(12) United States Patent
Vallée

(10) Patent No.: US 10,621,491 B2
(45) Date of Patent: Apr. 14, 2020

(54) METHOD FOR PREDICTING ADVERSE EVENTS FOR HOME HEALTHCARE OF REMOTELY MONITORED PATIENTS

(71) Applicant: ALAYA CARE INC., Montreal (CA)

(72) Inventor: Jonathan Vallée, Laval (CA)

(73) Assignee: ALAYA CARE INC., Montreal (CA)

( * ) Notice: Subject to any disclaimer, the term of this patent is extended or adjusted under 35 U.S.C. 154(b) by 599 days.

(21) Appl. No.: 15/175,637

(22) Filed: Jun. 7, 2016

(65) Prior Publication Data
US 2016/0378943 A1 Dec. 29, 2016

Related U.S. Application Data

(60) Provisional application No. 62/184,349, filed on Jun. 25, 2015.

(51) Int. Cl.
| | |
|---|---|
| *G06N 3/00* | (2006.01) |
| *G06N 3/08* | (2006.01) |
| *G16H 50/30* | (2018.01) |
| *G16H 40/63* | (2018.01) |
| *G16H 10/20* | (2018.01) |
| *G16H 10/60* | (2018.01) |
| *G06N 3/04* | (2006.01) |

(52) U.S. Cl.
CPC .............. *G06N 3/08* (2013.01); *G06N 3/04* (2013.01); *G16H 10/20* (2018.01); *G16H 10/60* (2018.01); *G16H 40/63* (2018.01); *G16H 50/30* (2018.01)

(58) Field of Classification Search
CPC ............ G06N 3/08; G06N 3/04; G16H 10/60; G16H 50/30; G16H 40/63; G16H 10/20; G06F 19/00

USPC .............................................................. 705/2
See application file for complete search history.

(56) References Cited

U.S. PATENT DOCUMENTS

| | | | |
|---|---|---|---|
| 8,630,966 B2 * | 1/2014 | Gage | G06N 3/082 706/25 |
| 8,751,257 B2 | 6/2014 | Amland et al. | |
| 8,949,082 B2 | 2/2015 | Farooq et al. | |
| 2009/0299929 A1 * | 12/2009 | Kozma | G06N 3/0454 706/25 |

(Continued)

OTHER PUBLICATIONS

Pierre Baldi, Kurt Hornik, Neural Networks and Principal Component Analysis: Learning from Examples Without Local Minima, 1989, Neural Networks, vol. 2 pp. 53-58 (Year: 1989).*

(Continued)

*Primary Examiner* — Robert A Sorey
*Assistant Examiner* — Kimberly A. Sass
(74) *Attorney, Agent, or Firm* — Benoit & Cote Inc.; Charles-André Caron

(57) ABSTRACT

There is described a method for dynamically computing a patient dynamic risk score indicative of an adverse event occurring on a given day. The method comprises obtaining clinical documentation data, socio-demographic data, answers to remote patient monitoring questionnaires, and vital signs data. The method further comprises using, in a feedforward artificial neural network, the clinical documentation data, the socio-demographic data, the answers to remote patient monitoring questionnaires and the vital signs data to compute the patient dynamic risk score indicative of a risk indicative of the adverse event occurring on a given day.

15 Claims, 5 Drawing Sheets

(56) References Cited

U.S. PATENT DOCUMENTS

| | | | | |
|---|---|---|---|---|
| 2011/0280863 | A1* | 11/2011 | Buhimschi | G01N 33/689 424/130.1 |
| 2011/0295621 | A1* | 12/2011 | Farooq | G06Q 10/10 705/3 |
| 2014/0304204 | A1* | 10/2014 | Cameron | G06F 19/3456 706/21 |
| 2015/0150514 | A1* | 6/2015 | Batchinsky | A61B 5/7275 600/301 |

OTHER PUBLICATIONS

Karthik Kalyan, Binal Jakhia,Ramachandra Dattatraya Lele, Mukund Joshi, and Abhay Chowdhary, Artificial Neural Network Application in the Diagnosis of Disease Conditions with Liver Ultrasound Images, 2014, Hindawi Publishing Corporation, Advances in Bioinformatics vol. 2014, 14 pages (Year: 2014).*

James Bergstra and Yoshua Bengio, Random Search for Hyper-Parameter Optimization, 2012, Journal of Machine Learning Research 13, pp. 281-305 (Year: 2012).*

Dialog machine translation of: Ermolov et. al., Method of Estimating Severity Degree and Prediction of Lethal Outcome in Patients With Combined Trauma and Continued Bleeding, (Published Apr. 27, 2015), RU 2549531 C1 (Year: 2015).*

* cited by examiner

| 9 | 10 | 11 | 12 |
|---|---|---|---|
| ID | Date | X | Event |
| 1 | 2015-05-01 | $x_1, ..., x_n$ | 0 |
| 1 | 2015-05-02 | $x_1, ..., x_n$ | 0 |
| 1 | 2015-05-03 | $x_1, ..., x_n$ | 0 |
| 1 | 2015-05-04 | $x_1, ..., x_n$ | 1 |
| 1 | 2015-05-05 | $x_1, ..., x_n$ | 0 |
| ⋮ | ⋮ | ⋮ | ⋮ |
| 1 | 2015-05-15 | $x_1, ..., x_n$ | 1 |
| 1 | 2015-05-16 | $x_1, ..., x_n$ | 0 |
| 1 | 2015-05-17 | $x_1, ..., x_n$ | 0 |
| 1 | 2015-05-18 | $x_1, ..., x_n$ | 0 |
| ⋮ | ⋮ | ⋮ | ⋮ |
| 1 | 2015-05-30 | $x_1, ..., x_n$ | 0 |

| 13 | 14 | 15 | 16 |
|---|---|---|---|
| ID | Days | X | Observed |
| 1 | 3 | $x_1, ..., x_n$ | 1 |
| 1 | 10 | $x_1, ..., x_n$ | 1 |
| 1 | 14 | $x_1, ..., x_n$ | 0 |

FIGURE 3

METHOD FOR PREDICTING ADVERSE EVENTS FOR HOME HEALTHCARE OF REMOTELY MONITORED PATIENTS

CROSS-REFERENCE TO RELATED APPLICATIONS

This application claims priority from US provisional patent application No. 62/184,349 filed on Jun. 25, 2015.

BACKGROUND

(a) Field

The present disclosure relates to the field of machine learning for predicting adverse events. More specifically, the disclosure relates to methods and systems applying machine learning in home healthcare systems.

(b) Related Prior Art

Patients that are being cared for by a home healthcare agency are often diagnosed with multiple chronic conditions. One of the main objectives of a home healthcare agency is to maintain patients at home, out of hospitals, for as long as possible. This improves the patient's quality of life and reduces the healthcare system's costs.

Remote patient monitoring (RPM) is an emerging technology that helps the home healthcare agencies manage a plurality of patients without intrusion in the patients' lives. RPM may work as follows:
1. The patient is provided with a tablet computer on which a RPM application is installed
2. The patient is provided with a number of vital sign self-monitoring Bluetooth devices such as, but not limited to:
   a) a Weight Scale;
   b) a Pulse Oximeter;
   c) a Thermometer;
   d) a Blood Pressure Cuff;
   e) a Blood Glucose Meter; and
   f) a physical activity tracking device;
3. Periodically (e.g., daily), the patient is asked to answer a questionnaire on the RPM application residing on the tablet computer:
   a) Questions are setup to be answered in a quantitative manner (e.g. Likert scale); and
   b) Vital signs measures are taken during the questionnaire; and
4. The data is transmitted to the home healthcare agency database.

The home healthcare database includes the patient's file that includes its clinical documentation and personal information. When an event, such as a hospital readmission or an emergency room visit occurs, a dated entry is made to the patient's file to keep a record thereof.

Generally, nurses are responsible for the monitoring of the RPM data and will take action when required, often on gut-feeling. Some systems enable the care workers to setup alerts based on ranges of values for patients' vital signs. For example, a low alert may be triggered if a patient's diastolic pressure is between 120 and 130, a medium alert between 130 and 140 and a high alert if it is above 140. This is usually done manually, patient by patient.

Other systems, such as expert systems, have encapsulated the care workers' knowledge in a set of rules that are applied to the data and that will make state predictions. The benefits of these systems are that care workers do not have to manually enter the rules themselves and that a lot of medical knowledge and best practices can be incorporated within them. The main issues with these systems are that they are static which means that they do not learn from new data and that they can only model linear functions based on an "if-then-else" set of rules.

U.S. Pat. No. 8,949,082, granted on Feb. 3, 2015 to Farooq et al. and U.S. Pat. No. 8,751,257, granted on Jun. 10, 2014 both provide methods and systems to generate risk score that are static. This resembles expert systems.

In contrast, machine learning is a field of science interested in the development of algorithms that can teach themselves and grow with new data. Usually, machine learning algorithms will get better as they are exposed to data. This becomes critical with the rapid pace of today's healthcare system data accumulation. Machine learning has been successfully applied to a number of industries such as finance, retail, and even healthcare.

One of the supervised learning algorithms that has been applied to medical data is survival analysis. Survival analysis algorithms are one of the first data mining algorithms that we know. Indeed, the first traces of the use of a survival algorithm applied to the insurance industry dates back to 1693 as discussed in "An Estimate of the Degrees of Mortality of Mankind, Drawn from Curious Tables of the Births and Funerals at the City of Breslaw", by Halley Edmond, Philosophical Transactions of the Royal Society of London, 17(196):576-610, 1693. Survival analysis models the time until an event occurs. An event is a variable of interest such as death, customer churn, or hospital readmission. Often, those algorithms are used to assess the difference in the effect of a variable, such as the use of a drug, between a test population and a control population's time until an event occurs. Statistically significant differences between the groups' time until an event occurs will tell the researcher if the use of the drug is beneficial. Those models are extremely useful in medical studies because they can cope with censored data, meaning that for some of the observations, the event will not be observed during the study period even though it might still happen in the future.

The Cox Proportional Hazard Model is a specialization of survival analysis and enables researchers to explore the relationships of covariates on a population's survival. It is also a useful model to estimate a hazard of death given a number of explanatory variables. Similarly, Frailty models are a specialization of Cox Proportional Hazard modes, but add a group aspect to the analysis. The assumption is that a group will share a propensity to risk that is different from other groups. Those models can be used to analyze recurring events for a patient, the patient being the group.

Another class of supervised learning algorithms is classification models. Classification models use the structure and labels of the data to learn to classify observations into groups. Some often used classification models are but are not limited to k-means, expectation maximization, logistic regression, and neural networks. Lately, neural networks have gained a lot of attention because of the performance they've achieved on a number of computer vision and natural language processing benchmarks.

With the recent interest of making the healthcare system shift to accountable care, home healthcare agencies are increasingly focusing on cost reduction, standardized care, and quality improvement. In order to achieve that goal, it is imperative to provide care workers with tools that can learn from data and grow with the patient base. What is thus needed is for the state-of-the-art technology to be introduced and adopted by home healthcare software.

The things that are needed to achieve cost reductions, standardized care, and quality improvement, will be put forth as solutions hereinbelow.

SUMMARY

There is disclosed herein a methodology of dynamically predicting remote monitoring patients' risk of experiencing an adverse event such as a hospital readmission or an emergency room visit a number of days before the occurrence of the event.

The present disclosure overcomes the problems identified herein by providing a methodology that dynamically estimates a probability of an event occurring in the next few days so that the care workers can try to prevent the event and maintain patients at home longer.

The approach uses a layered machine learning architecture to estimate:
1. a patient static risk score based on the patient's file and the changes thereto; and
2. a dynamic adverse event risk score based on the patient's file, static risk score and remote monitoring patient data.

According to an aspect of the invention, there is provided method for dynamically computing a patient dynamic risk score indicative of an adverse event occurring on a given day, the method comprising: obtaining clinical documentation data, socio-demographic data, answers to remote patient monitoring questionnaires, and vital signs data; using, in a feedforward artificial neural network, the clinical documentation data, the socio-demographic data, the answers to remote patient monitoring questionnaires and the vital signs data to compute the patient dynamic risk score indicative the adverse event occurring on a given day.

According to an embodiment, the feedforward artificial neural network comprises a multilayer perceptron (MLP) feedforward artificial neural network (ANN) to compute the patient dynamic risk score.

According to an embodiment, there is further provided obtaining vital signs' 1 and 2 days log ratios and using the vital signs' 1 and 2 days log ratios as an input feature vector to the MLP feedforward ANN.

According to an embodiment, using the multilayer perceptron (MLP) feedforward artificial neural network (ANN) comprises inputting formatted patient health-related data into an input layer of neurons, computing a linear combination of the input layer of neurons using weights and applying a sigmoid transformation at each neuron of a hidden layer, and computing a linear combination of the hidden layer using weights and applying a sigmoid transformation at each neuron of an output layer.

According to an embodiment, the weights for each neuron of the hidden layer and of the output layer are stored in the feedforward artificial neural network.

According to an embodiment, the stored weights for each neuron of the hidden layer and of the output layer are previously determined as those which optimize a weighted cost function.

According to an embodiment, there is further provided calculating a performance metric by summing a specificity and sensitivity and ranking models trained by the MLP feedforward ANN based on the summing.

According to an embodiment, there is further provided using, in a hazard model algorithm, the clinical documentation data and the socio-demographic data to compute a patient static risk score.

According to an embodiment, the hazard model algorithm comprises a frailty model to compute the patient static risk score.

According to another aspect of the invention, there is provided a method of providing an alert from a machine learning server over a network, the method comprising: providing a user interface application to a patient for installation on a remote subscriber computer for inputting patient health-related data; providing a feedforward artificial neural network application trained with previous health-related data relating to a plurality of patients for installation on the machine learning server, the feedforward artificial neural network application being trained to classify risk indicative of an adverse event occurring on a given day based on non-linear patterns of the patient health-related data; providing an alert application for installation on at least one of the remote subscriber computer and a caregiver computer to provide an alert on a device associated to the at least one of the remote subscriber computer and a caregiver computer; receiving the patient health-related data at the machine learning server sent from the remote subscriber computer over a communication network, the machine learning server comprising a processor and a memory that stores format specifications for the feedforward artificial neural network application, wherein the processor formats the patient health-related data in a format ready for the feedforward artificial neural network; feeds the formatted patient health-related data into the feedforward artificial neural network application; runs the feedforward artificial neural network application to compute the patient dynamic risk score indicative of a risk indicative of an adverse event occurring on a given day; generates an alert signal formatted for network communication if the patient dynamic risk score is above a threshold; transmits the alert signal over the communication network to the at least one of the remote subscriber computer and the caregiver computer on which the alert application is installed, wherein the alert activates the alert application to cause the alert application to display on the at least one of the remote subscriber computer and the caregiver computer on which the alert application is installed.

According to an embodiment, the patient health-related data comprising clinical documentation data, socio-demographic data, answers to remote patient monitoring questionnaires, and vital signs data.

According to an embodiment, the processor runs the feedforward artificial neural network application comprising a multilayer perceptron (MLP) feedforward artificial neural network (ANN).

According to an embodiment, the processor runs the multilayer perceptron (MLP) feedforward artificial neural network (ANN) which comprises inputting the formatted patient health-related data into an input layer of neurons, computing a linear combination of the input layer of neurons using weights and applying a sigmoid transformation at each neuron of a hidden layer, and computing a linear combination of the hidden layer using weights and applying a sigmoid transformation at each neuron of an output layer.

According to an embodiment, the weights for each neuron of the hidden layer and of the output layer are stored in the feedforward artificial neural network application.

According to an embodiment, the stored weights for each neuron of the hidden layer and of the output layer are previously determined as those which optimize a weighted cost function.

According to an embodiment, there is further provided calculating a performance metric by summing a specificity and sensitivity and ranking models trained by the MLP feedforward ANN based on the summing.

According to another aspect of the invention, there is provided a method of classifying a data set by a machine learning server sampled over a network from a remote subscriber computer, the method comprising: providing the remote subscriber computer comprising an input for inputting patient health-related data; formatting the patient health-related data into a transmission-ready format; transmitting over a communication network the formatted patient health-related data from the remote subscriber computer to a remote machine learning server; providing a feedforward artificial neural network application for installation on the machine learning server, the feedforward artificial neural network application being used to classify risk indicative of an adverse event occurring on a given day; receiving the formatted patient health-related data at the machine learning server sent, the machine learning server comprising a processor and a memory that stores format specifications for the feedforward artificial neural network application, wherein the processor formats the patient health-related data in a format ready for the feedforward artificial neural network; inputs the formatted patient health-related data into the feedforward artificial neural network application; runs the feedforward artificial neural network application to classify the patient health-related data as having a Boolean value of risk indicative of the adverse event occurring on a given day; generates a signal formatted for network communication comprising the Boolean value of risk; transmits the signal over the communication network to at least one of the remote subscriber computer and a caregiver computer on which an application is installed to interpret the Boolean value of risk in the signal, wherein the signal activates a generation of an alert on the at least one of the remote subscriber computer and the caregiver computer.

According to an embodiment, the patient health-related data comprising clinical documentation data, socio-demographic data, answers to remote patient monitoring questionnaires, and vital signs data.

According to an embodiment, the processor runs the feedforward artificial neural network application comprising a multilayer perceptron (MLP) feedforward artificial neural network (ANN).

According to an embodiment, the processor runs the multilayer perceptron (MLP) feedforward artificial neural network (ANN) which comprises inputting the formatted patient health-related data into an input layer of neurons, computing a linear combination of the input layer of neurons using weights and applying a sigmoid transformation at each neuron of a hidden layer, and computing a linear combination of the hidden layer using weights and applying a sigmoid transformation at each neuron of an output layer.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 3 comprises two tables showing a transformation from an input dataset to a frailty model data structure according to an embodiment;

It will be noted that throughout the appended drawings, like features are identified by like reference numerals.

DETAILED DESCRIPTION

Figure 1:
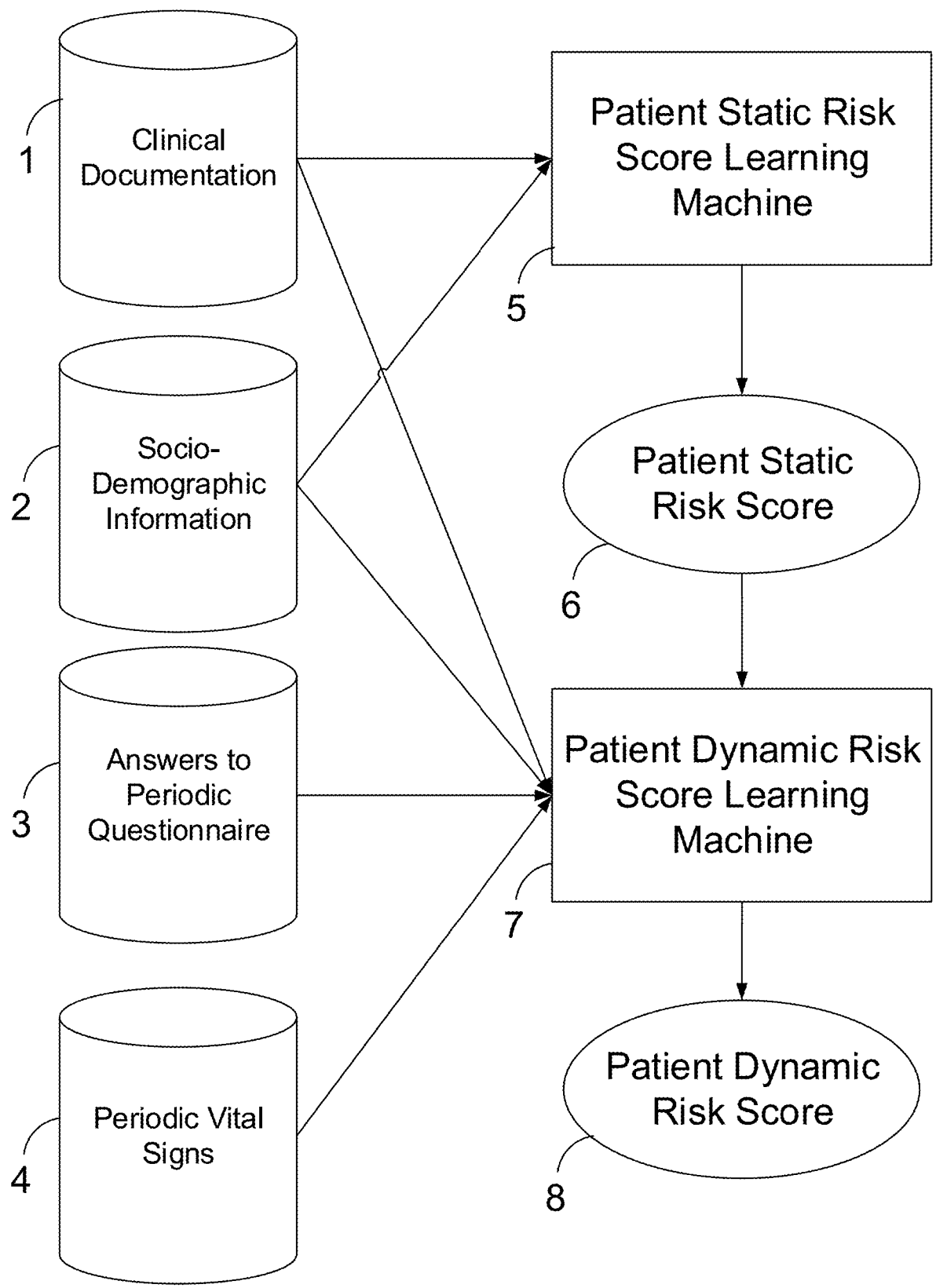
FIG. 1 is a schematic diagram showing learning algorithms data sources and an architecture for the system for predicting adverse events for home healthcare of remotely monitored patient according to an embodiment.

FIG. 1 shows the architecture of the system for predicting adverse events for home healthcare of remotely monitored patient according to an embodiment. Clinical Documentation Database 1, Socio-Demographic Database 2, Answers to Periodic Questionnaire Database 3 and Periodic Vital Signs Database 4 are examples of data sources that the system uses. Other data sources can be included would they be available.

In this example, Clinical Documentation Database 1 comprises the clinical documentation data source that includes, but is not limited to, the patient medical history, prescribed drugs and medical assessments. The data in the Clinical Documentation Database 1 are therefore long term data which do not vary on a day-to-day basis.

Socio-Demographic Database 2 comprises the patient socio-demographic information that includes, but is not limited to, the patient age, sex, race, and height. The data in the Socio-Demographic Database 2 are therefore long term data which do not vary on a day-to-day basis, by contrast with the data in the following databases.

Answers to Periodic Questionnaire Database 3 comprise the answers to the remote patient monitoring application questionnaire. These answers may or may not be in quantitative form. If not, it is necessary to perform a qualitative to quantitative transformation with the use of tools like, but not limited to, sentiment analysis.

Answers to Periodic Questionnaire Database 3 are given by the patient on a remote subscriber computing device 100. The remote subscriber computing device 100 may take the form of a tablet computer, a desktop or laptop computer, a smartphone, or any other network-connected device including watches, appliances, home automation systems, etc. The remote subscriber computing device 100 comprises a user interface, such as a touchscreen, as screen and keyboard, or other user-interactive display by which a user may enter information about their health state through the periodic questionnaire to fill in the database 3 with appropriate information. The remote subscriber computing device 100 further comprises a memory and a processor for storing data and instructions and for executing the instructions, respectively. The instructions may take the form of an application 5 installed on the remote subscriber computing device 100, through which the user interface is implemented.

Periodic Vital Signs Database 4 comprises the vital signs that are being gathered by the remote patient monitoring application. The questionnaire is being answered on a periodic basis (e.g., daily, twice a week, etc.) defined by the patient's care manager. The vital signs can include, without limitation: weight, blood oxygen, pulse, blood pressure, and temperature.

Periodic Vital Signs Database 4 can be measured by dedicated tools. For example, the weight, blood oxygen, pulse, blood pressure and temperature should be measured by a balance, an oxygen meter, a person or a pulse-meter, a sphygmomanometer and a thermometer, respectively, or instruments integrating these specific tools. As noted, some values such as the pulse may be measured by a person. The tools for data measurement can be in network communication (either wired or wireless, e.g., Bluetooth) with, or plugged into, the remote subscriber computing device 100 to transmit the measured data to the application installed on the remote subscriber computing device 100. Alternatively, the measurements can be noted by the patient or a caregiver and inputted manually through the user interface of the application into the remote subscriber computing device 100.

Figure 5:
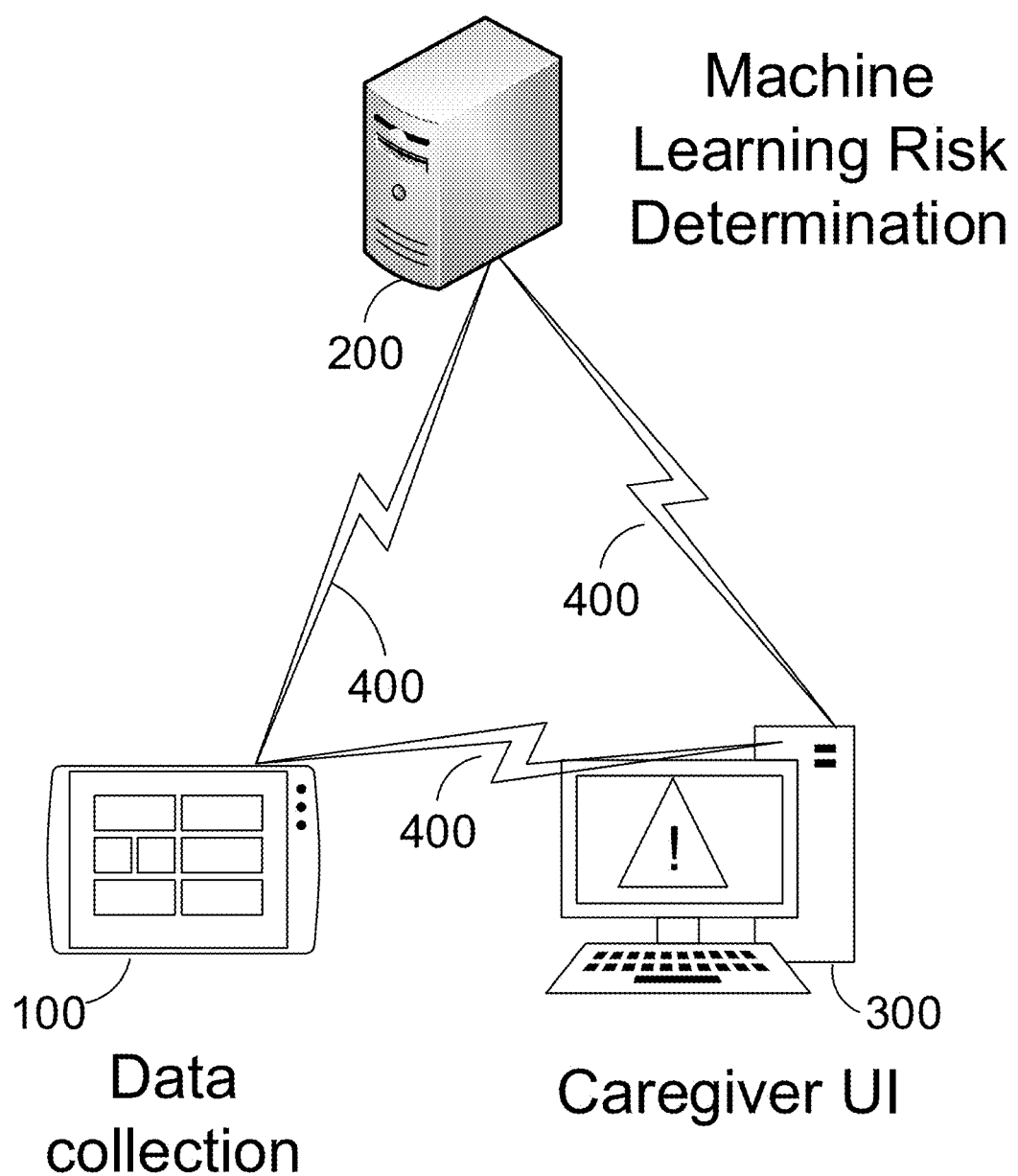
FIG. 5 is a block diagram illustrating the devices for patient data collection, machine learning risk determination and caregiver user interface in network communication, according to an embodiment.

As shown in FIG. 5, the remote subscriber computing device 100 is in network communication (either wired or wireless) with a server 200. A network 400 which is usual for this type of communication is the internet. The server 200 is remotely located with respect to the remote subscriber computing device 100. The server 200 receives data from the remote subscriber computing device 100, either passively or after having queried the remote subscriber computing device 100 for such data, via the network 400. The server 200 has a memory for storing data and a processor for executing instructions which may be stored on the memory of the server or elsewhere. These instructions implement a feedforward artificial neural network application to classify the patient health-related data as having a value of risk (which can be continuous and compared to a risk threshold, or Boolean, for example) indicative of the adverse event occurring on a given day. The server 200, or machine learning server, is thus adapted to perform machine learning as described in more detail below.

Patient Static Risk Score Learning Machine 5 estimates a Patient Static Risk Score 6 for a patient. The higher the risk score, the higher the likelihood that the patient will experience adverse events while on the RPM program. The Patient Static Risk Score 6 can be computed with different algorithms but we will exemplify the computation by using a frailty model.

The frailty model is an extension of the Cox Proportional Hazard model that includes a family frailty term. This term controls for patients' recurring events. Since our events of interest are not death, but rather hospital readmission and emergency room visits, the probability of a patient experiencing more than one event during its time on the program is greater than 0.

The model estimates the hazard ratio at time t based on the patient's ID and a matrix of covariates. Let $\lambda(t)$ be the hazard at time t, j(i) means that individual i belongs to family j, $\overline{\omega}$ be the frailty for family j, X a covariate matrix of dimension n×p and $\beta$ a vector of regression coefficients. Based on "Penalized Survival Models and Frailty", by Terry M Therneau et al., Journal of computational and graphical statistics, 12(1):156-175, 2003, the frailty model equation is:

$$\lambda_i(t) = \lambda_0(t)\overline{\omega}_{j(i)} e^{X_i\beta}$$

In order to fit this model, the input data must be transformed to the frailty model requirements.

FIG. 3 illustrates two example tables. The first table represents the raw data input. "ID" Column 9 comprises the variable that will be used as the family indicator, "Date" Column 10 comprises the date at which the observation has been captured, "Matrix X" Column 11 comprises the static explanatory variables that will be used as a covariate matrix, "Event" Column 12 comprises the indicator variable that captures if the patient experienced an adverse event on that day (i.e., the corresponding date from "Date" Column 10).

The second table represents the transformed data used to fit the frailty model. "ID" Column 13 comprises the family of the data row, "Days" Column 14 comprises the number of days of the observation, "Matrix X" Column 15 comprises the covariate matrix, and "Observed" Column 16 comprises an indication of whether an event has been observed. Unless the patient's last day on the RPM program is an event, the last row of the patient's transformed dataset will be censored, meaning that y will be equal to 0.

Furthermore, the number of days of the observation found in the "Days" Column 14 is calculated as follows. Referring to FIG. 3, the patient is admitted to the program on May 1$^{st}$ of 2015 and experiences its first event on May 4$^{th}$ of the same year. This translates to the first transformed row's "Days" column 14 to be 3 and "Observed" Column 16 to be 1.

The model is trained on a historical transformed dataset. Every time a patient experiences an event or is being discharged from the program, the transformed dataset is updated and the model is retrained.

Figure 2:
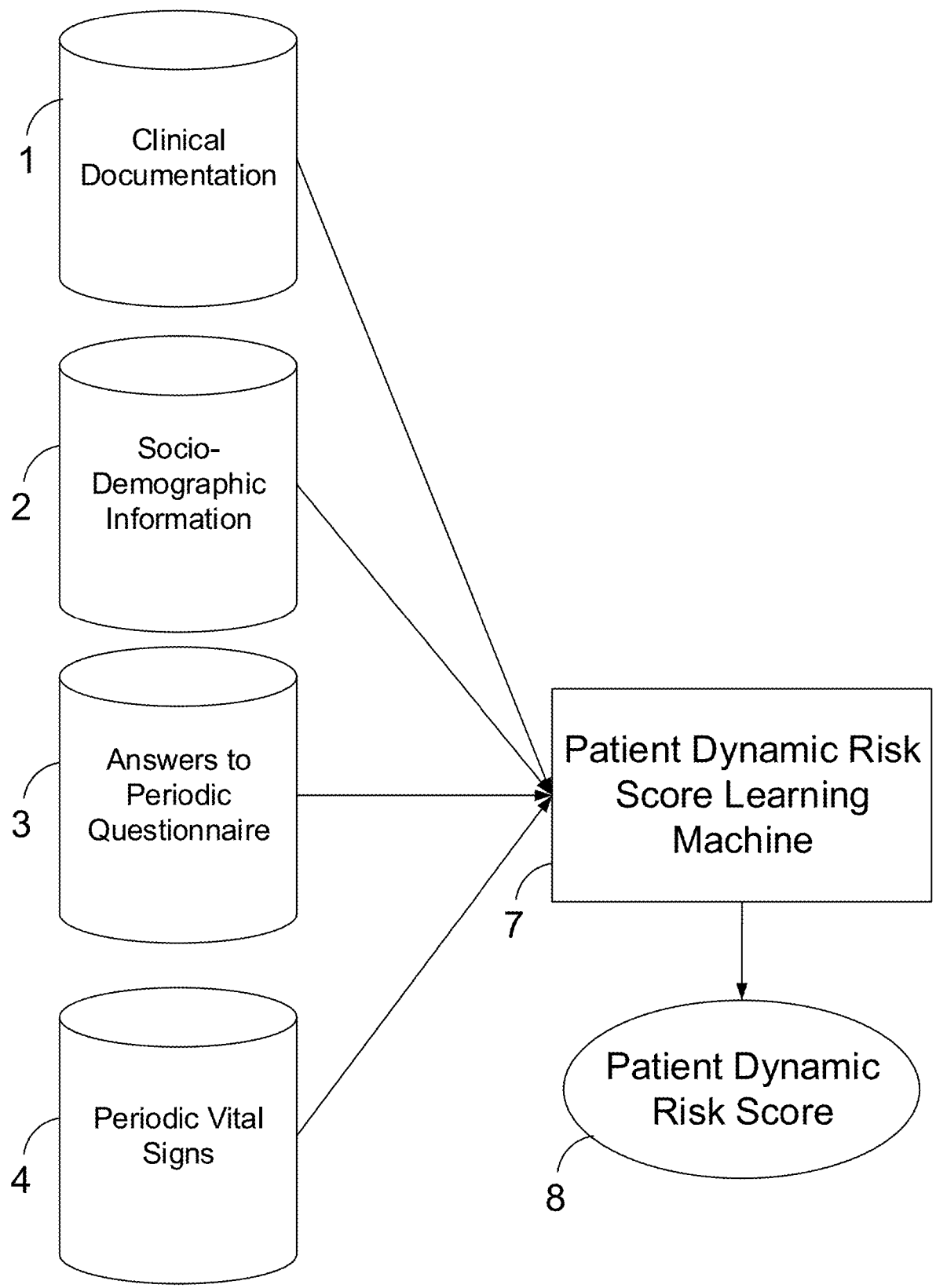
FIG. 2 is a schematic diagram showing learning algorithms data sources and an architecture for the system for predicting adverse events for home healthcare of remotely monitored patient according to another embodiment.

Then, according to an embodiment and as shown in FIG. 1, once a patient is admitted to the program, a Patient Static Risk Score 6 can be computed from its clinical documentation (from Clinical Documentation Database 1), socio-demographic data (from Socio-Demographic Database 2), and other data when available from the trained model in Patient Static Risk Score Learning Machine 5 as exp(X$\beta$). In another embodiment and as shown in FIG. 2, the Patient Static Risk Score 6 is not computed.

Patient Dynamic Risk Score Learning Machine 7 performs the computation for the step of training a classification model to discriminate between days that will lead to an event and days that are riskless and hence determines the Patient Dynamic Risk Score 8. Many models can be used to achieve this objective, but we will exemplify it with a multilayer perceptron (MLP) feedforward artificial neural network (ANN).

Figure 4:
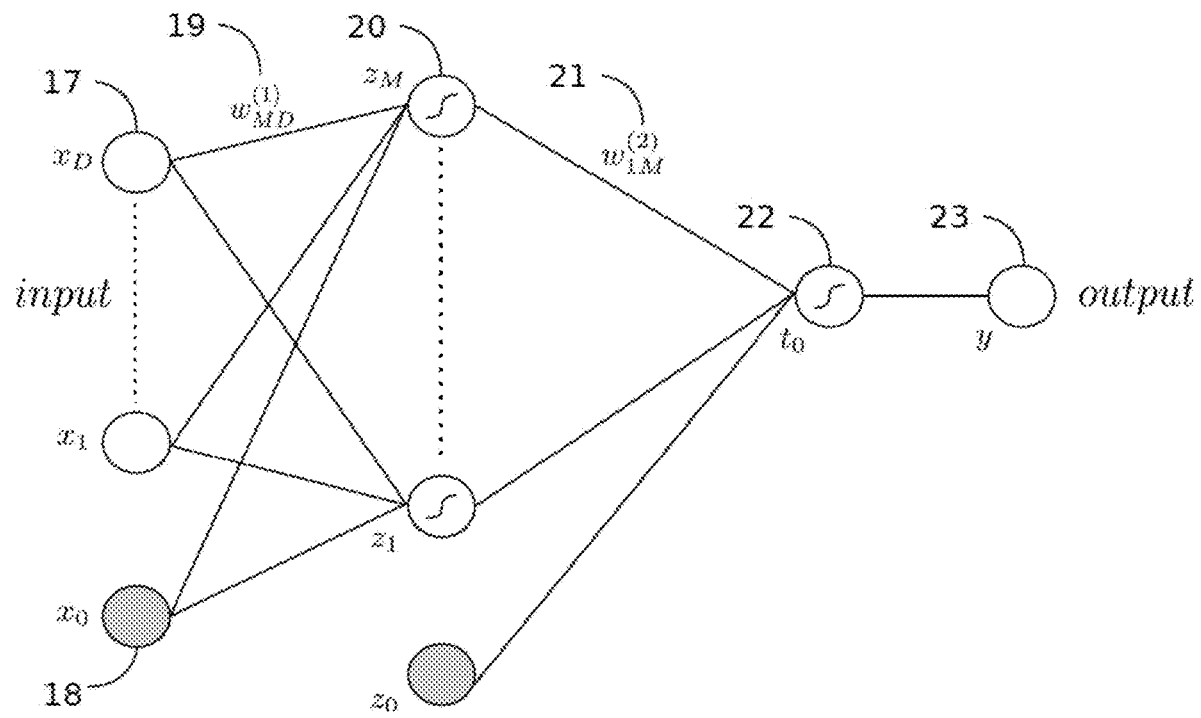
FIG. 4 is a node diagram showing an embodiment of an architecture of the multilayer perceptron (MLP) feedforward artificial neural network (ANN) used to dynamically predict the patient's risk of experiencing an adverse event in the next few days.

FIG. 4, inspired by the publication entitled "Pattern Recognition and Machine Learning" Vol. 4, by Christopher M. Bishop et al, New York, 2006, illustrates the configuration of the ANN used to perform the classification task. It is a single hidden layer ANN with a sigmoid activation function on its hidden layer and a second sigmoid function on its output layer. This ANN is trained using a stochastic gradient descent optimization algorithm.

The ANN comprises and Input Layer 17. This is a feature vector extracted from, but not limited to, the different data sources in Clinical Documentation Database 1, Socio-Demographic Database 2, Answers to Periodic Questionnaire Database 3 and Periodic Vital Signs Database 4 and Patient Static Risk Score 6 computed by Patient Static Risk Score Learning Machine 5. The data can be formatted to be inputted into the Input Layer 17, for example they can be normalized or put in vector form. In addition to these raw features, different data augmentation procedure such as the 1 and 2 day log ratios can be computed to help the classification algorithm capture latent data structure. For example, let t be a date, t−1 be the day before, and $x_t$ be the variable of interest at time t, the 1 day log ratio is computed as follows: $\log(x_t/x_{t-1})$. The 1 and 2 days log ratios will help the classification algorithm by modeling variations in the variables.

In order to reduce the input data dimensionality, a feature extraction algorithm can be run on the dataset. Randomized Principal Component Analysis (RPCA), as suggested in the publication entitled "Finding structure with randomness: Probabilistic algorithms for constructing approximate matrix decompositions", by Nathan Halko et al., SIAM review, 53(2):217-288, 2011, is an exemplary way of reducing the input space while preserving enough of the variance to explain the data. Other methods for reducing the input space known to those skilled in the art may also be used.

The following algorithm may be used to train a number of RPCA in order to preserve p of the data variance.

---
Algorithm 1: Randomized PCA - Number of principal components selection
---

Data: dataset, p
Results: Principal components that retain at least p of the variance
1   initialization
2   for i ← 1 to data.numberOfColumns do
3     result = RPCA(dataset, nComponents = i);
4     if results.variance ≥ p then
5       return results;

---

For example, if p is set to 0.95, then a number of features describing at least 95% of the variance will be used as the input dataset. The RPCA model is then kept to subsequently transform the prediction requests.

Matrix 19 and Matrix 21 are the parameters of the ANN. Matrix 19 is a matrix of weights that links the Input Layer 17 to the Hidden Layer 20. Matrix 21 is a matrix of weights that links the Hidden Layer 20 to Output Layer 22.

Hidden Layer 20 and Output Layer 22 both compute the linear combination of the preceding layer's neuron values by the weight matrix and apply a sigmoid transformation to it (symbolized as a long 's' in the nodes of the layers 20, 22). Let $\alpha$ be the result of the linear combination of the preceding layer's neuron values and the associated weight matrix, the sigmoid transformation is obtained by $1/(1+e^{-\alpha})$.

Gray Nodes, including Bias Node 18, are multiplied by a weight of 1 during the linear combination. Their values are optimized with the model parameters.

The ANN target variable (t) is an indicator variable that is set to 1 if an event occurs in d days. For example, if d equals 2 and t is the day that an event occurs, $t_{t-2}$ and $t_{t-1}$ will be equal to 1. This will enable the ANN to be trained to classify as risky the days before an event, thus help the care workers to prevent the event.

The ANN is optimized based on a weighted cost function. The first portion of the cost function is the negative log-likelihood and the second portion is the L1 regularization penalty. The cost function equation is written as follows:

$$E(W) = a\left(-\sum_{n=1}^{N}\{t_n \ln y_n + (1-t_n)\ln(1-y_n)\}\right) + b\left(\frac{\lambda}{2}W^{(2)T}W^{(2)}\right)$$

where $t_n$ is the $n^{th}$ target, $y_n$ is the $n^{th}$ predicted value, a and b are weights and $\lambda$ is the L1 regularization coefficient.

The training data should be separated in three different sets: the training, the validation, and the test sets. Typically, the proportions are of 0.7, 0.2, and 0.1. This data architecture enables to assess the model's performance on out-of-sample data, meaning data on which training has not occurred. Other types of validation can also be used, such as k-fold cross-validation, including 10-fold cross-validation, which comprises dividing a data set in k=10 different sets and using 9 out of 10 data sets for training and the remaining one for validation. This is then performed repeatedly by permuting data sets.

The forward propagation equation to compute the predicted value y (Output 23 and Patient Dynamic Risk Score 8) is given by:

$$y(X,W) = \sigma(W^{(2)}z\sigma(W^{(1)}X))$$

where $$\sigma = 1/(1+e^{-\alpha})$$

A cutoff point is selected so that the classification error is minimized on the validation set. Thus, let $\rho$ be the cutoff point, y be the predicted probability of t, the target=1, then the predicted class is 1 if $y > \rho$.

An ANN is governed by a number of hyperparameters that are optimized by grid search. This means that a list of values is provided for each hyperparameter, that a model is trained with every combination of the hyperparameters subjects to the provided list and that the best model based on a given performance metric gets selected.

For example, let TP be true positives, FP be false positives, TN be true negatives, and FN be false negatives. Those values can be illustrated by a confusion matrix.

|  |  | Predicted Value | |
|---|---|---|---|
|  |  | 0 | 1 |
| Actual | 0 | TN | FP |
| Value | 1 | FN | TP |

A performance metric $\phi$ may be the sum of the specificity ($1^{st}$ term in the equation) and the sensitivity ($2^{nd}$ term in the equation) if the case of misclassifying a 0 is as bad as misclassifying a 1:

$$\phi = \frac{TP}{TP+FN} + \frac{TN}{TN+FP}$$

For example, the confusion matrix of a situation in which nursing staff takes decision can be as follows (experimental result):

| Alert level | TP | FP | TN | FN | Sensitivity | Specificity | SBM ($\phi$) |
|---|---|---|---|---|---|---|---|
| Low | 240 | 40,080 | 35,832 | 207 | 54% | 47% | 1.01 |
| Medium | 126 | 18,847 | 57,065 | 321 | 28% | 75% | 1.03 |
| High | 109 | 12,197 | 63,715 | 338 | 24% | 84% | 1.08 |
| All | 340 | 54,384 | 21,528 | 107 | 76% | 28% | 1.04 |

For example, the confusion matrix of a situation in which the system makes determinations can be as follows (experimental result):

| TP | FP | TN | FN | Sensitivity | Specificity | SBM (φ) |
|---|---|---|---|---|---|---|
| 376 | 25,006 | 50,906 | 71 | 84% | 67% | 1.51 |

The experimental results presented above demonstrate the benefits of having identified the nonlinear nature of the relation between the monitored physiological measures and the risk to be assessed. Sensitivity increases from 76% to 84%, which means that more positive events are predicted. Specificity increases from 28% to 67%, which means that less negative events are marked as positive.

Once the determination has been made by the server 200 using machine learning for identifying the risk while taking into account the nonlinear nature of the risk versus a plurality of factors, there is formatted and outputted a signal from the server 200 to a caregiver computing device 300 and/or to the remote subscriber computing device 100. This signal should be formatted for network communication by which it is communicated to the other device(s). It carries the value of the risk determination, or the Boolean value of the risk determination, thereby comprising an alarm instruction if necessary.

The caregiver computing device 300 comprises a display through which the result of the determination can be shown to the caregiver (e.g., nursing staff). This display can also be a user interface through which the caregiver can enter or query information about the patient or make queries about the risk as determined by the server 200. The remote subscriber computing device 100 can also comprise similar elements.

According to an embodiment, if the risk is determined as a positive value on a given day, the alert is sent from the server 200 to the caregiver computing device 300 so that the caregiver receives the alert notification, as shown in FIG. 5. The caregiver comprises anyone of medical or nursing staff or other healthcare professionals, or the alert service provider as a suitable intermediary for the actual caregiver. This alert can be an instruction to display a visual indication on the user interface of the computing device 300 as to the nature of the alert regarding a given patient. The instruction could also result in other types of notifications, such as sound notifications, or the triggering of other types of applications on the caregiver computing device 300. The instructions can make the computing device 300 further communicate automatically with another device such as a phone, smartphone, pager, and the like.

The system adapted to treat the alert signal received from the server 200 can be considered as an alert application which receives the alert signal, treats it, including extracting risk values therein, and eventually performs operations depending on the risk value such as generating an alert (display, sound, etc.) or sending instructions to other applications within the device or to other devices.

According to an embodiment, the caregiver computing device 300 is not a desktop or laptop computer but a mobile device such as a phone, smartphone, pager, and the like, that can communicate over a network such as the internet or a phone network, either wired or wireless.

According to an embodiment, the caregiver receives the notification through the caregiver computing device 300 and may approve, via its user interface, the validity of the alert. This approval takes the form of a signal travelling from the caregiver computing device 300 to the server 200 through the appropriate type of network 400. The server 200 can then send a notification via the network 400 to the remote subscriber computing device 100 to notify the patient, or alternatively the caregiver computing device 300 can then send a notification via the network 400 to the remote subscriber computing device 100. The exact network connections required for the system depend on how the communications are implemented.

According to another embodiment, once a determination of positive risk of event is made by the server 200, the server 200 sends an alert to both the remote subscriber computing device 100 and the caregiver computing device 300. In this case, no network connection between the remote subscriber computing device 100 and the caregiver computing device 300 is needed.

According to an embodiment, the server 200 may be the computer associated with the caregiver computing device 300.

Therefore, even though various embodiments are possible, there are provided a device for the patient, a device for the caregiver, and a device for performing the risk determination taking into account the nonlinear nature of the risk-determining factors. The network connectivity between these devices may vary, but at the end of the day each device should be connected at least indirectly to each other device (i.e., the network connection may be direct or via another device). The remote subscriber computing device 100, the server 200 and the caregiver computing device 300, as well as their communication network channels to ensure the flow of information via signals, are therefore essential for performing the invention.

This system for remote patient monitoring takes into account the nonlinear contribution of the factors (health-related data of the patient) in determining the risk of occurrence of an event during a given day, with greater quality of prediction than systems which use a linear combination of these factors to predict events. Moreover, this system is advantageous over expert systems (i.e., systems with many science-based rules implemented) in that the system described herein is self-adaptive: once new data are fed into the server 200 over time, the values of the weights and other adjustable variables of the neural network can be changed automatically to better suit reality. The system therefore improves itself over time without having to modify rules therein, thereby improving event prediction for remote patient monitoring over the network 400 and also improving the overall quality of alert signals sent over the network 400.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of providing an alert from a machine learning server over a network, the method comprising:
providing a user interface application to a patient for installation on a remote subscriber computer for inputting patient health-related data;
computing a static frailty risk of a patient based on the patient health-related data as inputted;
providing a feedforward artificial neural network application trained with previous health-related data relating to a plurality of patients for installation on the machine learning server, the feedforward artificial neural network application being trained to classify a patient dynamic risk score based on non-linear patterns of the patient health-related data;
providing an alert application for installation on at least one of the remote subscriber computer and a caregiver computer to provide an alert on a device associated to the at least one of the remote subscriber computer and a caregiver computer;

receiving the patient health-related data at the machine learning server sent from the remote subscriber computer over a communication network, the machine learning server comprising a processor and a memory that stores format specifications for the feedforward artificial neural network application, wherein the processor formats the patient health-related data in a format ready for the feedforward artificial neural network, comprising computing a logarithmic ratio of a present-day patient dynamic risk score over a previous-day patient dynamic risk score to include in the formatted patient health-related data;

feeds the formatted patient health-related data into the feedforward artificial neural network application;

runs the feedforward artificial neural network application to compute the patient dynamic risk score indicative of a risk indicative of an adverse event occurring on a given day within a number of next days, excluding a present day, in view of the patient health-related data, of changes to the patient health-related data, of the logarithmic ratio of the present-day patient dynamic risk score over the previous-day patient dynamic risk score, and of the static frailty risk;

generates an alert signal formatted for network communication if the patient dynamic risk score is above a threshold;

transmits the alert signal over the communication network to the at least one of the remote subscriber computer and the caregiver computer on which the alert application is installed and dynamically adjusts weights of the feedforward artificial neural network application, without changing the feedforward artificial neural network application, in view of the formatted patient health-related data and actual adverse event occurring on the given day, wherein the alert activates the alert application to cause the alert application to display on the at least one of the remote subscriber computer and the caregiver computer on which the alert application is installed.

2. The method of claim 1, wherein the patient health-related data comprise clinical documentation data, socio-demographic data, answers to remote patient monitoring questionnaires, and vital signs data.

3. The method of claim 2, wherein the processor runs the feedforward artificial neural network application comprising a multilayer perceptron (MLP) feedforward artificial neural network (ANN).

4. The method of claim 3, wherein the processor runs the multilayer perceptron (MLP) feedforward artificial neural network (ANN) which comprises inputting the formatted patient health-related data into an input layer of neurons, computing a linear combination of the input layer of neurons using weights and applying a sigmoid transformation at each neuron of a hidden layer, and computing a linear combination of the hidden layer using weights and applying a sigmoid transformation at each neuron of an output layer.

5. The method of claim 4, wherein the weights for each neuron of the hidden layer and of the output layer are stored in the feedforward artificial neural network application.

6. The method of claim 5, wherein the stored weights for each neuron of the hidden layer and of the output layer are previously determined as those which optimize a weighted cost function.

7. The method of claim 6, further comprising training models of the feedforward artificial neural network application with a plurality of hyperparameters optimized by grid search, and calculating a performance metric of a model of the feedforward artificial neural network application by summing a specificity and sensitivity.

8. The method of claim 1, wherein when the processor feeds the formatted patient health-related data into the feedforward artificial neural network application, the processor performs feature extraction algorithm using Randomized Principal Component Analysis.

9. A method of classifying a data set by a machine learning server sampled over a network from a remote subscriber computer, the method comprising:

providing the remote subscriber computer comprising an input for inputting patient health-related data;

formatting the patient health-related data into a transmission-ready format;

transmitting over a communication network the formatted patient health-related data from the remote subscriber computer to a remote machine learning server;

providing a feedforward artificial neural network application for installation on the machine learning server, the feedforward artificial neural network application being used to classify a dynamic risk;

receiving the formatted patient health-related data at the machine learning server, the machine learning server comprising a processor and a memory that stores format specifications for the feedforward artificial neural network application, wherein the processor computes a static frailty risk of a patient based on the patient health-related data as inputted;

formats the patient health-related data in a format ready for the feedforward artificial neural network, comprising computing a logarithmic ratio of a present-day patient dynamic risk score over a previous-day patient dynamic risk score to include in the formatted patient health-related data;

inputs the formatted patient health-related data into the feedforward artificial neural network application;

runs the feedforward artificial neural network application to classify the patient health-related data as having a Boolean value for the dynamic risk indicative of an adverse event occurring on a given day within a number of next days, excluding a present day, in view of the patient health-related data, of changes to the patient health-related data, of the logarithmic ratio of the present-day patient dynamic risk score over the previous-day patient dynamic risk score, and of the static frailty risk;

generates a signal formatted for network communication comprising the Boolean value of risk;

transmits the signal over the communication network to at least one of the remote subscriber computer and a caregiver computer on which an application is installed to interpret the Boolean value of risk in the signal; and dynamically adjusts weights of the feedforward artificial neural network application, without changing the feedforward artificial neural network application, in view of the formatted patient health-related data and actual adverse event occurring on a given day, wherein the signal activates a generation of an alert on the at least one of the remote subscriber computer and the caregiver computer.

10. The method of claim 9, wherein the patient health-related data comprises clinical documentation data, socio-demographic data, answers to remote patient monitoring questionnaires, and vital signs data.

11. The method of claim 10, wherein the processor runs the feedforward artificial neural network application comprising a multilayer perceptron (MLP) feedforward artificial neural network (ANN).

12. The method of claim 11, wherein the processor runs the multilayer perceptron (MLP) feedforward artificial neural network (ANN) which comprises inputting the formatted patient health-related data into an input layer of neurons, computing a linear combination of the input layer of neurons using weights and applying a sigmoid transformation at each neuron of a hidden layer, and computing a linear combination of the hidden layer using weights and applying a sigmoid transformation at each neuron of an output layer.

13. The method of claim 9, further comprising training models of the feedforward artificial neural network application with a plurality of hyperparameters optimized by grid search.

14. The method of claim 13, further comprising calculating a performance metric of one of the models of the feedforward artificial neural network application by summing a specificity and sensitivity.

15. The method of claim 9, wherein when the processor inputs the formatted patient health-related data into the feedforward artificial neural network application, the processor performs feature extraction algorithm using Randomized Principal Component Analysis.

* * * * *